US008133219B2

(12) United States Patent
Sato

(10) Patent No.: US 8,133,219 B2
(45) Date of Patent: Mar. 13, 2012

(54) HIGH FREQUENCY OPERATION APPARATUS AND HIGH FREQUENCY OPERATION METHOD

(75) Inventor: Taisuke Sato, Hachioji (JP)

(73) Assignee: Olympus Medical Systems Corp., Tokyo (JP)

(*) Notice: Subject to any disclaimer, the term of this patent is extended or adjusted under 35 U.S.C. 154(b) by 641 days.

(21) Appl. No.: 12/246,870

(22) Filed: Oct. 7, 2008

(65) Prior Publication Data
US 2010/0087817 A1   Apr. 8, 2010

(51) Int. Cl.
A61B 18/18 (2006.01)
(52) U.S. Cl. .......................... 606/40; 606/51
(58) Field of Classification Search .............. 606/48, 606/49, 50, 51, 52, 205, 206, 207, 208, 209, 606/210, 211, 32–47
See application file for complete search history.

(56) References Cited

U.S. PATENT DOCUMENTS

| | | | | |
|---|---|---|---|---|
| 5,443,463 A * | 8/1995 | Stern et al. | | 606/51 |
| 6,152,923 A * | 11/2000 | Ryan | | 606/51 |
| 6,203,541 B1 * | 3/2001 | Keppel | | 606/38 |
| 7,491,201 B2 * | 2/2009 | Shields et al. | | 606/51 |
| 2005/0101951 A1 * | 5/2005 | Wham et al. | | 606/51 |
| 2006/0064086 A1 * | 3/2006 | Odom | | 606/51 |
| 2006/0116675 A1 * | 6/2006 | McClurken et al. | | 606/51 |
| 2006/0224158 A1 * | 10/2006 | Odom et al. | | 606/51 |
| 2008/0009860 A1 * | 1/2008 | Odom | | 606/51 |
| 2008/0039836 A1 * | 2/2008 | Odom et al. | | 606/51 |

FOREIGN PATENT DOCUMENTS

| | | |
|---|---|---|
| JP | 8-505544 | 6/1996 |
| JP | 2000-342594 | 12/2000 |
| JP | 2004-160083 | 6/2004 |
| JP | 3564141 | 6/2004 |
| JP | 2005-501609 | 1/2005 |
| JP | 2005-124476 | 5/2005 |
| JP | 2006-521181 | 9/2006 |
| WO | WO 94/11059 | 5/1994 |
| WO | WO 96/00036 | 1/1996 |
| WO | WO 03/020339 A2 | 3/2003 |
| WO | WO 2004/086944 A2 | 10/2004 |
| WO | WO 2007/100067 A1 | 9/2007 |

* cited by examiner

Primary Examiner — Kevin C Sirmons
Assistant Examiner — William Carpenter
(74) Attorney, Agent, or Firm — Scully, Scott, Murphy & Presser, P.C.

(57) ABSTRACT

A high frequency operation apparatus includes: a treatment section provided with electrodes for performing treatment of a living tissue; a switch section connected to each of the electrodes and switching conduction of the electrodes to configure paired electrodes from the electrodes; a power supply section for supplying high frequency power to the living tissue via the paired conductive electrodes; a biological information measuring section for sequentially measuring biological information; a determining section for determining if the measured values of biological information are within a predetermined range; and a control section for performing control so that the high frequency power is supplied to the living tissue by using only the paired electrodes corresponding to the measure value determined as being within the predetermined range.

14 Claims, 8 Drawing Sheets

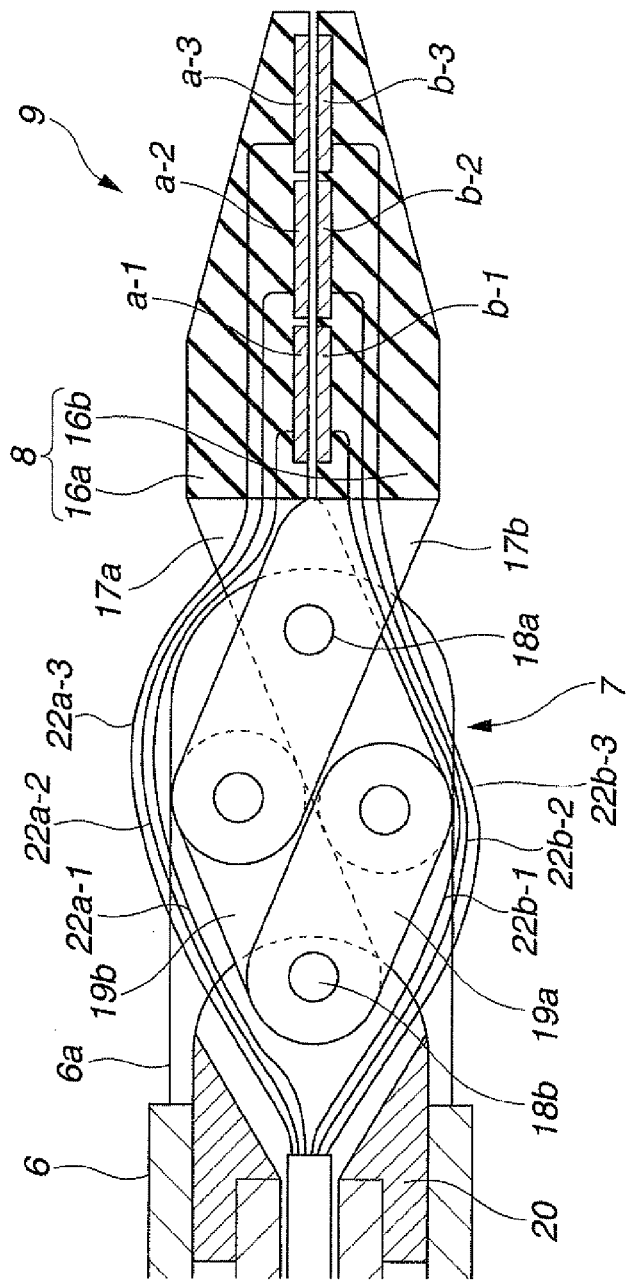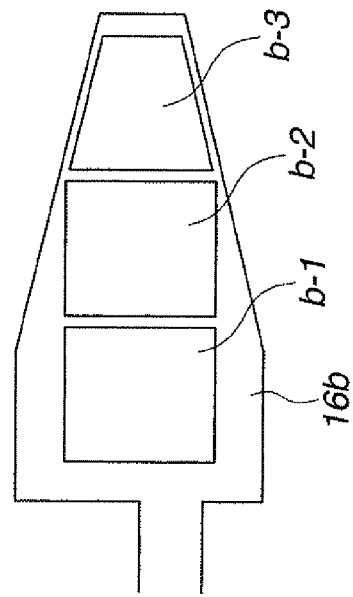

FIG.5
○: OPEN  —: CLOSE
| PROCEDURE No. | ELECTRODE | | | | | | DETERMINATION RESULT |
|---|---|---|---|---|---|---|---|
| | a-1 | a-2 | a-3 | b-1 | b-2 | b-3 | |
| 1 | — | ○ | ○ | — | ○ | ○ | |
| 2 | ○ | — | ○ | ○ | — | ○ | |
| 3 | ○ | ○ | — | ○ | ○ | — | |
FIG.7
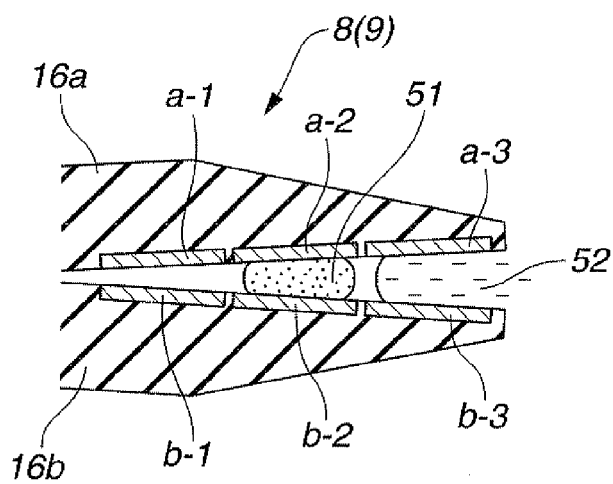
FIG.8
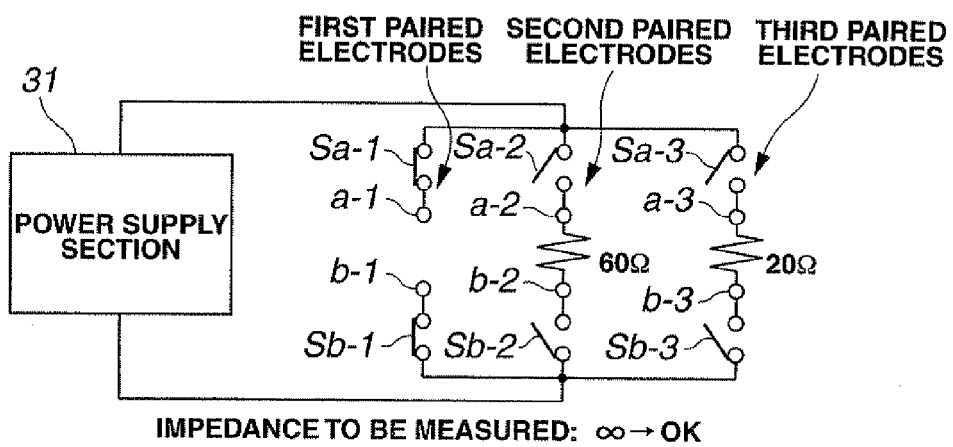
IMPEDANCE TO BE MEASURED: ∞ → OK

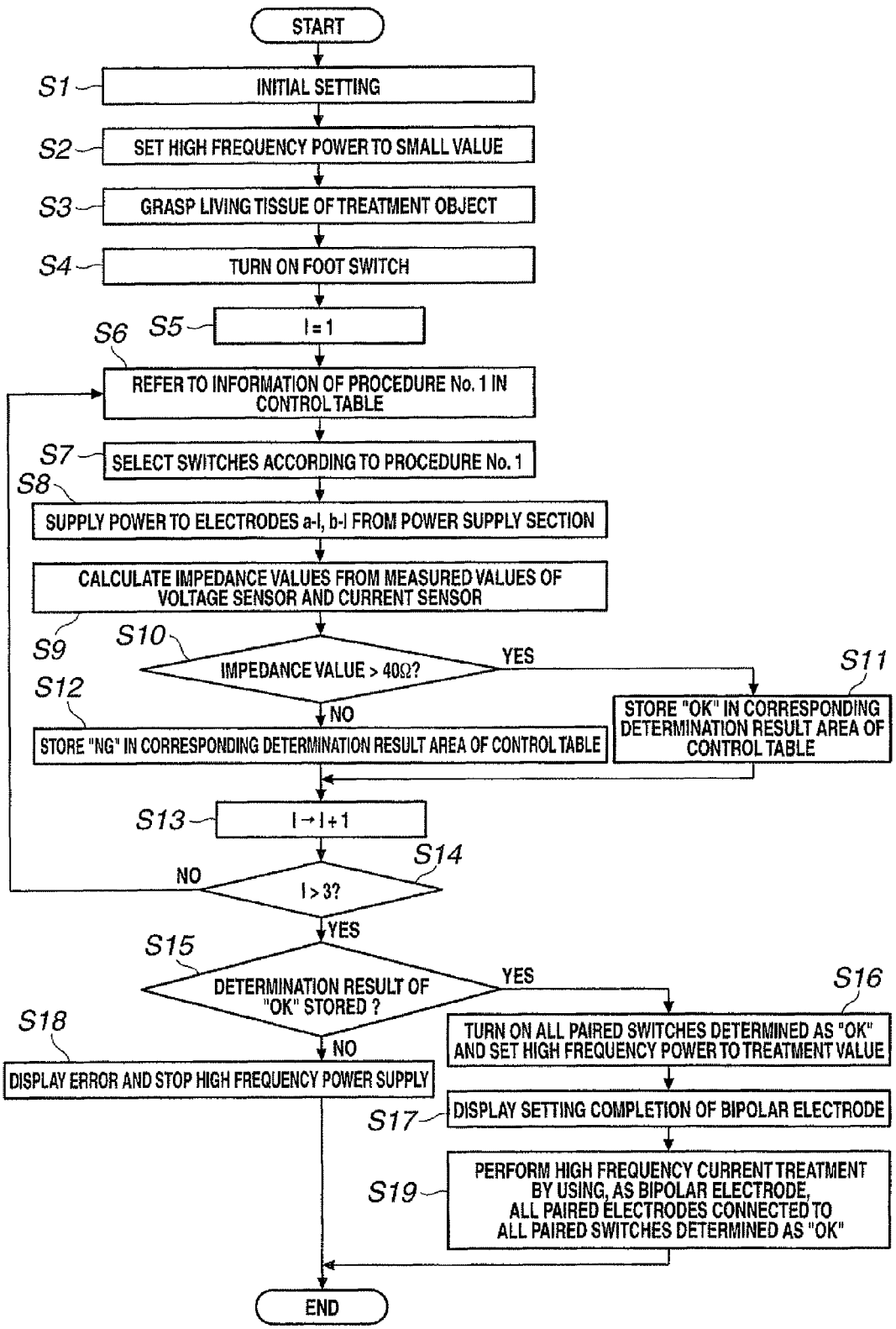

IMPEDANCE TO BE MEASURED: 60Ω→OK

IMPEDANCE TO BE MEASURED: 20Ω→NG

APPLY HIGH FREQUENCY CURRENT
BY USING FIRST PAIRED ELECTRODES AND
SECOND PAIRED ELECTRODES

HIGH FREQUENCY OPERATION APPARATUS AND HIGH FREQUENCY OPERATION METHOD

BACKGROUND OF THE INVENTION

1. Field of the Invention

The present invention relates to a high frequency operation apparatus and a high frequency operation method, in which a high frequency operation is performed by using paired bipolar electrodes.

2. Description of the Related Art

There is a high frequency operation apparatus configured to perform a high frequency operation by using a high frequency treatment instrument provided with a bipolar electrode at a distal end treatment section thereof and by making a frequency current flow from the bipolar electrode to a living tissue as a treatment object. There is a case where a treatment for occluding a blood vessel is performed by using the bipolar electrode which forms the treatment section in the high frequency operation apparatus.

In the case where the treatment for occluding the blood vessel is performed in this way, a treatment is performed in such a way that a high frequency current is applied in a state where the blood vessel is grasped by the facing bipolar electrodes, and that the blood vessel is occluded by Joule heat generated at the time when the high frequency current flows through the living tissue.

Note that the high frequency current passes through a portion having a lower impedance as an electrical characteristic. Further, the impedance value of blood is lower than that of a living tissue, such as a blood vessel.

When the high frequency operation is performed by a treatment section 71 provided with facing bipolar electrodes 72 and 72 in a preceding example, there may be, for example as shown in FIG. 14, a case where a large amount of blood 74 is adhered around a blood vessel 73 grasped by the bipolar electrodes.

When a high frequency current is applied in this state, the impedance of the blood 74 is lower than that of the blood vessel 73 as explained above, and hence a larger high frequency current flows into the blood 74 than into the blood vessel 73. Thereby, there is a possibility that the blood 74 is scorched and stuck to the bipolar electrodes 72 and 72 due to a rapid increase in temperature of the blood 74 by Joule heat, so as to make it difficult to smoothly perform the treatment to occlude the blood vessel 73.

Further, when the treatment is to be performed by grasping the blood vessel 73 between the bipolar electrodes 72 and 72 similarly as shown in FIG. 15, there may also be a case where the distal end portion of the bipolar electrodes 72 and 72 are immersed in the blood 74.

Also in this case, similarly to the above described case, there is a possibility that when a high frequency current is applied, a larger amount of current is made to flow into the blood 74, to cause the blood 74 to be scorched and stuck to the distal end portion of the bipolar electrodes 72 and 72.

For this reason, a high frequency operation apparatus and a high frequency operation method are desired, which are capable of reducing the scorching and sticking of the blood even in the state where the blood is adhered to the bipolar electrode, and which are capable of smoothly performing a high frequency operation, such as a treatment to occlude the blood vessel.

SUMMARY OF THE INVENTION

A high frequency operation apparatus according to the present invention includes:

a treatment section configured to perform a treatment of a living tissue as a treatment object;

a plurality of electrodes provided at the treatment section;

a switch section connected to each of the plurality of electrodes and configured to switch between conduction and cut-off of the plurality of electrodes so as to configure paired electrodes from the plurality of electrodes;

a power supply section configured to supply high frequency power to the living tissue via the switch section and the paired electrodes which are made conductive by the switch section;

a biological information measuring section configured to sequentially measure biological information of the living tissue in such a way that a plurality of mutually different sets of paired electrodes are formed by the switching of the switch section, and that the high frequency power is supplied via each of the plurality of sets of the paired electrodes from the power supply section;

a determining section configured to determine, by referring to a reference value, whether or not the measured values of biological information, which are measured for the plurality of sets by the biological information measuring section, are within a predetermined range; and a control section configured to perform control so that the high frequency power is supplied to the living tissue by using, as a bipolar electrode, only the paired electrodes corresponding to the measured value which is determined by the determining section as being within the predetermined range.

According to the present invention, a high frequency operation method is also provided for performing a high frequency operation to a living tissue by selectively setting a bipolar electrode used for treatment from a plurality of sets of paired electrodes respectively provided on a pair of treatment members which are opened or closed and which are provided at a distal end of a high frequency treatment instrument, the high frequency operation method including:

a grasping step of grasping a living tissue as a treatment object by the pair of treatment members;

an electrode selection step of sequentially selecting one set of paired electrodes from the plurality of sets of paired electrodes which are respectively provided on the mutually facing surfaces of the pair of treatment members;

a power supply step of supplying high frequency power to the living tissue, which is grasped by the pair of treatment members, via the sequentially selected one set of paired electrodes;

a biological information measurement step of sequentially measuring biological information at the time when the high frequency power is supplied via the sequentially selected one set of paired electrodes;

a determination step of determining, by a comparison with a reference value, whether or not the value of the sequentially measured biological information is within a set range; and a control step of performing control so that the high frequency power is supplied to the living tissue by using, as one bipolar electrode, only the paired electrodes corresponding to the measured value which is determined by the determination step as being within the set range.

BRIEF DESCRIPTION OF THE DRAWINGS

FIG. 2 is a sectional view showing a configuration of a peripheral portion of a treatment section provided with a bipolar electrode, in a high frequency treatment instrument;

FIG. 3 is a plan view showing shapes of a plurality of electrodes provided on one of treatment members configuring the treatment section;

FIG. 5 is a figure showing switching control contents in a switch section control table;

FIG. 6 is a flow chart showing an example of a control method for performing a high frequency operation according to the present embodiment;

FIG. 7 is a figure explaining an operation in FIG. 6;

FIG. 8 is a figure showing an equivalent circuit in the case where an impedance is measured by a first paired electrodes in the state shown in FIG. 7;

DETAILED DESCRIPTION OF THE PREFERRED EMBODIMENTS

In the following, each embodiment according to the present invention will be described with reference to the accompanying drawings.

First Embodiment

Figure 1:
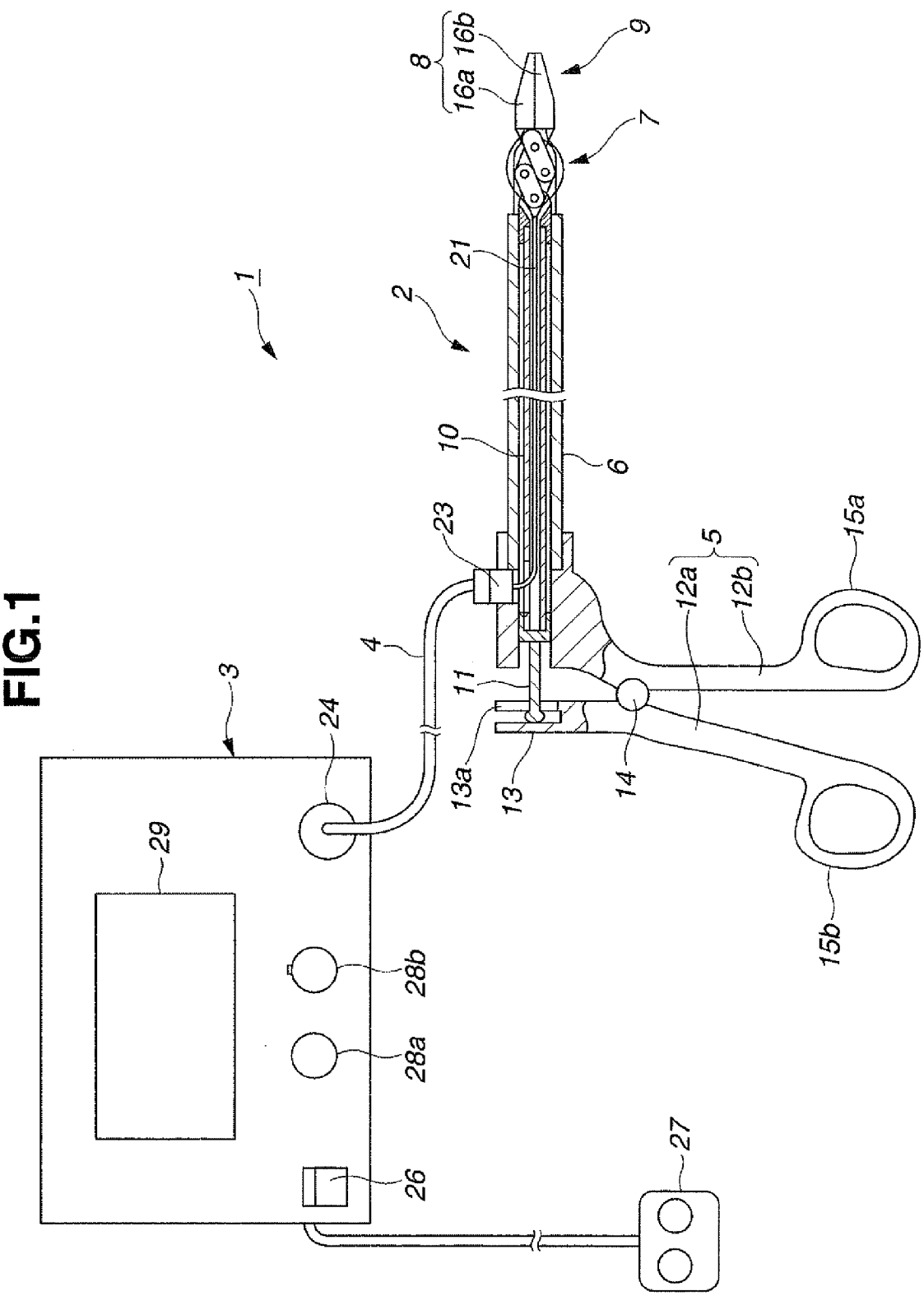
FIG. 1 is a figure showing an entire configuration of a high frequency operation apparatus according to a first embodiment of the present invention.

As shown in FIG. 1, a high frequency operation apparatus 1 according to a first embodiment of the present invention includes a high frequency treatment instrument 2 which performs a high frequency operation, and a high frequency power supply apparatus 3 which is connected to the high frequency treatment instrument 2 via a cable 4 and which supplies high frequency power for performing the high frequency operation to the high frequency treatment instrument 2.

The high frequency treatment instrument 2 includes an operation section 5 which is grasped and operated by an operator, a sheath 6 which is extended from the upper end side of the operation section 5, and a treatment section 8 which is provided at the distal end of the sheath 6 via a link mechanism 7, and which performs a treatment of a high frequency operation by applying a high frequency current to a living tissue.

A slide pipe 10 is inserted into the sheath 6, and the rear end of the slide pipe 10 is connected via a connection shaft 11 to a connection shaft bearing section 13 at the upper end of one of handles 12a and 12b which form the operation section 5. Note that in the connection shaft bearing section 13 is provided a slit 13a which allows the rear end side of the connection shaft 11 to pass therethrough and which prevents a ball at the rear end of the connection shaft 11 from passing therethrough.

The handles 12a and 12b are rotatably connected to each other by a pivotal support section 14, and finger hook sections 15a and 15b are provided on the lower end side of the handles 12a and 12b.

Thus, when the operator performs an operation to open or close the finger hook sections 15a and 15b, the upper end side of the handles 12a and 12b is moved in the direction opposite to the direction of the operation. By performing the above described operation, the operator is able to push the slide pipe 10 to the forward side, or to move the slide pipe 10 to the rear side.

A pair of treatment members 16a and 16b, which configure the treatment section 8, are connected to the distal end of the slide pipe 10 via the link mechanism 7 for opening or closing the treatment section 8.

Therefore, the operator is able to open or close the pair of treatment members 16a and 16b by performing the operation for opening or closing the handles 12a and 12b so as to drive the link mechanism 7 connected to the slide pipe 10 which is advanced and retracted. Thereby, the operator is able to grasp, for example, a blood vessel, which is a living tissue as a treatment object, by two mutually facing inner surface portions of the pair of treatment members 16a and 16b which are opened or closed.

Note that the state shown in FIG. 1 is a state where the handles 12a and 12b are closed. When the operation to open the handles 12a and 12b is performed in this state, the slide pipe 10 is moved forward, so as to enable the pair of treatment members 16a and 16b to be opened via the link mechanism.

The pair of treatment members 16a and 16b are formed of an insulating member. As shown in FIG. 2, a plurality of sets of paired electrodes a-1 and b-1; a-2 and b-2; a-3 and b-3 are provided, as a bipolar electrode section 9, on the two facing inner surface portions of the pair of treatment members 16a and 16b.

The treatment members 16a and 16b have a shape formed in such a way that a substantially conically shaped insulating member, obtained by cutting the outer peripheral surface of a columnar insulating member into a tapered shape, is bisected by a surface passing through the central axis of the insulating member. The rear end sides of the treatment members 16a and 16b are respectively connected to distal end link pieces 17a and 17b which configure the link mechanism 7.

The distal end link pieces 17a and 17b are rotatably supported by a pin 18a provided at a distal end member 6a which is fixed at the distal end of the sheath 6. The rear ends of the distal end link pieces 17a and 17b are respectively connected to rear end link pieces 19a and 19b via rotatable connecting sections.

Further, the rear ends of the rear end link pieces 19a and 19b are rotatably supported by a pin 18b provided at a pipe distal end member 20 which is fixed to the distal end of the slide pipe 10.

Note that the outer diameter of the pipe distal end member 20 is fitted to the inner diameter of the sheath 6 so that the pipe distal end member 20 is slid and moved together with the slide pipe 10 with respect to the sheath 6.

On the distal end side of the pipe distal end member 20 is provided an opening, through which signal lines 22a-1 to 22a-3 and 22b-1 to 22b-3 configuring a cable 21 inserted into the slide pipe 10 are extended to the distal end side. The signal lines 22a-1 to 22a-3 and 22b-1 to 22b-3 are respectively connected to a plurality of sets of paired electrodes, specifically three sets of paired electrodes a-1 and b-1; a-2 and b-2; a-3 and b-3, which configure the bipolar electrode section 9.

On the two facing inner surfaces of the paired treatment members 16a and 16b, for example, three sets of paired electrodes a-1 and b-1; a-2 and b-2; a-3 and b-3 are provided so as to be separated from each other along the longitudinal direction of the treatment members 16a and 16b.

Note that FIG. 3 shows shapes of the three electrodes b-1, b-2 and b-3 provided on the treatment member 16b. The three electrodes a-1, a-2 and a-3 provided on the treatment member 16a have the same shapes as those of the three electrodes b-1, b-2 and b-3. That is, above the three electrodes b-1, b-2 and b-3 on the paper surface of FIG. 3, the three electrodes a-1, a-2 and a-3 having the same shape are provided so as to face the three electrodes b-1, b-2 and b-3, respectively.

In this way, in the present embodiment, on the two facing inner surface portions of the paired treatment members 16a and 16b which are opened or closed, the three sets of paired electrodes a-1 and b-1; a-2 and b-2; a-3 and b-3 are provided so that each set of the paired electrodes face each other.

Further, it is configured such that the high frequency power can be supplied, from the high frequency power supply apparatus 3 shown in FIG. 1, to one or more sets of the paired electrodes selected, as bipolar electrodes actually used for treatment, from the three sets of paired electrodes a-1 and b-1; a-2 and b-2; a-3 and b-3 which configure the bipolar electrode section 9.

As shown in FIG. 1, the rear end of the cable 21 inserted into the slide pipe 10 is connected to a connector 23 which is provided, for example, at the upper end of the handle 12b. A connector 24 at the other end of the cable 4, one end of which is connected to the connector 23, is detachably connected to a connector receptacle which outputs the high frequency power of the high frequency power supply apparatus 3.

A foot switch 27 for turning on (conduction) and turning off (cut off) the output of high frequency power is connected to the high frequency power supply apparatus 3 in addition to a power switch 26. The operator is able to supply the high frequency power to the side of the bipolar electrode section 9 or to stop the supply of the high frequency power by performing an operation of stepping on the foot switch 27 by a foot.

Further, a power set button 28a for setting a value of high frequency power to be outputted is provided on the front surface of the high frequency power supply apparatus 3, so that the operator is able to perform the high frequency operation by setting the value of high frequency power to a value suitable for the treatment.

Further, in the present embodiment, a (bipolar) electrode setting operation mode is prepared in which a bipolar electrode suitable for performing the treatment is automatically selectively set in the state where the level of the high frequency power is set sufficiently smaller than that of the high frequency power actually used for the treatment.

On the front surface of the high frequency power supply apparatus 3, a selection switch 28b is provided for selecting an operation mode, such as a treatment operation mode in which the operator manually sets a bipolar electrode in accordance with the operation in the electrode setting operation mode or without the operation in the electrode setting operation mode and then performs the treatment with set high frequency power, and an operation mode in which the operator makes a bipolar electrode automatically selectively set in the electrode setting operation mode and then performs the treatment in the treatment operation mode.

Therefore, the operator is able to smoothly perform the treatment, which is intended to be performed by the operator, by selecting the operation mode by the selection switch 28b.

Further, on the front surface of the high frequency power supply apparatus 3 is provided a display section 29 which displays a set power value and various kinds of information.

Figure 4:
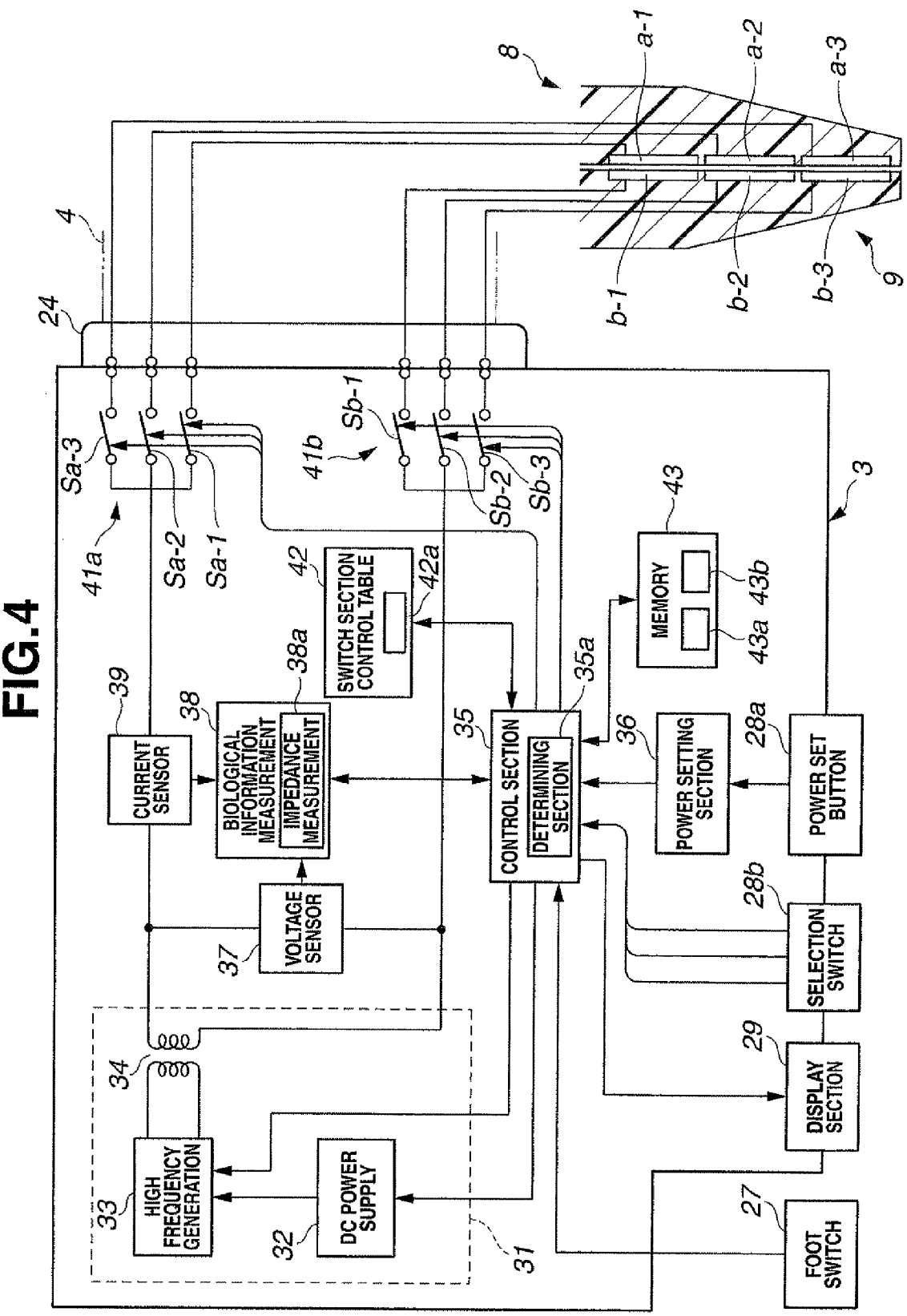
FIG. 4 is a figure showing a configuration of a high frequency power supply apparatus and a connection system between the high frequency power supply apparatus and the bipolar electrode section to which high frequency power is supplied.

FIG. 4 shows an internal configuration of the high frequency power supply apparatus 8.

As shown in FIG. 4, the high frequency power supply apparatus 3 outputs high frequency power from a high frequency power supply section (hereinafter referred to as power supply section) 31. The power supply section 31 includes a DC power supply circuit 32, a high frequency generating circuit 33 configured to generate a high frequency signal by the DC power supplied from the DC power supply circuit 32, and an output transformer 34 configured to supply the high frequency signal, as high frequency power, to the load side from the secondary winding side insulated from the primary winding side of the output transformer 34.

The DC power supply circuit 32 and the high frequency generating circuit 33 are connected to a control section 35 which performs overall control of the high frequency operation apparatus 1 including the high frequency power supply apparatus 3.

Further, the control section 35 is connected to the foot switch 27 and a power setting section 36 which sets a high frequency power value.

In correspondence with an operation of the foot switch 27, the control section 35 controls ON/OFF of DC power supplied from the DC power supply circuit 32 to the high frequency generating circuit 33.

Further, the power setting section 36 outputs information on the power value set by the power set button 28a to the control section 35. According to the power value information from the power setting section 36, the control section 35 controls the power value of DC power supplied from the DC power supply circuit 32 to the high frequency generating circuit 33, and controls the amplitude, or the like, of the high frequency signal generated by the high frequency generating circuit 33. Then, the control section 35 performs control so that the value of high frequency power outputted from the power supply section 31 becomes the set value.

Further, a signal (mode signal) of an operation mode selected by the selection switch 28b is also inputted into the control section 35. When the foot switch 27 is turned on, the control section 35 controls the operation of each section of the high frequency power supply apparatus 3 according to the signal of selected mode.

A voltage sensor 37 is connected between two output terminals of the power supply section 31. The voltage sensor 37 detects a high frequency signal voltage between the two output terminals of the power supply section 31. The voltage sensor 37 outputs information of the detected voltage value to a biological information measuring section 38 which measures (or calculates) biological information. The biological information measuring section 38 is configured by an impedance measuring section 38a in the present embodiment.

Further, one of two output terminals of the power supply section 31 is connected to one side of contacts of a switch section 41a via a current sensor 39 inserted in series between the one of the two output terminals and the one side of contacts, and the other of the two output terminals is directly connected to one side of contacts of a switch section 41b. The other sides of the contacts of the switch section 41a and the other sides of the contacts of the switch section 41b are connected to the connector receptacle, respectively.

The current sensor 39 outputs detected current value information to the biological information measuring section 38.

The impedance measuring section 38a which configures the biological information measuring section 38 measures (or calculates) an impedance value as biological information from the inputted voltage and current values. Note that the voltage sensor 37 and the current sensor 39 are capable of, for example, detecting a voltage value and a current value in synchronization with each other. Thus, even when the phases of the voltage and the current are different from each other, the impedance measuring section 38a is capable of accurately measuring the load side impedance.

The impedance value, as biological information, calculated by the impedance measuring section 38a is inputted into the control section 35.

The switch section 41a has three switches Sa-1, Sa-2 and Sa-3, and the switch section 41b has three switches Sb-1, Sb-2 and Sb-3.

Note that the three switches Sa-1, Sa-2 and Sa-3 or three switches Sb-1, Sb-2 and Sb-3 may be configured by a multiplexer.

The paired switch sections 41a and 41b are configured so as to enable the high frequency signal to be selectively applied to the three sets of paired electrodes a-1 and b-1; a-2 and b-2; a-3 and b-3 which configure the bipolar electrode section 9 provided in the above described treatment section 8.

That is, when the connector 24 is connected to the connector receptacle, the three switches Sa-1, Sa-2 and Sa-3 are connected to the three electrodes a-1, a-2 and a-3 via the cable 4, respectively. Also, the three switches Sb-1, Sb-2 and Sb-3 are connected to the three electrodes b-1, b-2 and b-3 via the cable 4.

Further, the control section 35 is connected to a switch section control table 42 in which a procedure for conduction/cut off or closing (ON)/opening (OFF) of the six switches configuring the switch sections 41a and 41b is stored.

The control section 35 refers to the procedure information in the switch section control table 42 in the case of automatically setting the electrodes used for treatment on the basis of the above described electrode setting operation mode.

When performing treatment of a living tissue, and more specifically when performing treatment to occlude a blood vessel, the control section 35 performs closing/opening control, that is, ON/OFF control of the switch sections 41a and 41b, according to the procedure information written beforehand in the switch section control table 42.

A specific example of the procedure is shown, for example, in FIG. 5. As shown in FIG. 5, only one set of paired switches of the three sets of paired switches Sa-1 and Sb-1; Sa-2 and Sb-2; Sa-3 and Sb-3 are sequentially opened (OFF) and then closed (ON) according to the procedures No. 1, and No. 2 and No. 3.

Further, while performing the ON/OFF control of the switch sections 41a and 41b according to the procedures, the control section 35 acquires the impedance values calculated from the information measured by the biological information measuring section 38, specifically, calculated from the measured values. Then, the control section 35 stores the acquired impedance value information, for example, in a measured value storage area 43a in a memory 43.

Further, in a reference value storage area 43b in the memory 43, reference values are stored beforehand as determination impedance information for determining whether or not a living tissue (specifically blood) different from the living tissue as the treatment object exists between the paired electrodes.

In the present embodiment, the following is stored, as the determination impedance information: an impedance value $Z_{th}$ (40Ω in the following description) which is used as a reference value and which is set to an impedance value between the impedance of the blood vessel as the living tissue as the treatment object and the impedance of blood smaller than the impedance of the blood vessel.

Then, the control section 35 compares the impedance value acquired from the measured value with the impedance value $Z_{th}$ as the reference value, to determine whether or not the closed paired switches (in other words, the paired electrodes electrically connected to the paired switches) are used for actual treatment.

That is, when the acquired impedance value is smaller than the impedance value $Z_{th}$, the control section 35 determines that an object which is not the treatment object, for example, blood, exists between the paired electrodes connected to the paired switches, and determines that the paired electrodes (that is, the paired switches) are not used for the treatment.

In the case where the object is not the treatment object, for example, in the case of blood, the high frequency loss for the supplied high frequency power is larger than that of the living tissue as the treatment object, and hence the temperature of the blood rapidly rises due to Joule heat, so that the blood is scorched and stuck to the electrode section. Therefore, when the treatment is actually performed, it is effective to prevent the high frequency power (for the treatment) from being supplied to the paired electrodes to which the blood is stuck.

Thus, in order to realize such operation, the control section 35 performs the determination as described above.

On the other hand, when the acquired impedance value is larger than the impedance value $Z_{th}$, the control section 35 determines that the living tissue as the treatment object exists between the paired electrodes connected to the paired switches, and determines that the paired electrodes may be used for the treatment.

In this way, the control section 35 has a function of a determining section 35a configured to determine whether or not the paired electrodes are suitable to be used as the bipolar electrode used for the treatment, by comparing the impedance value acquired by the measurement with the reference value, in other words, to determine whether or not the impedance value acquired by the measurement is within a predetermined range.

Note that in the present embodiment, it is configured such that even when nothing exists between the paired electrodes, the control section 35 determines that the paired electrodes may be used for the treatment. In this case, it may also be configured such that the control section 35 determines that the paired electrodes are not used for the treatment. In order to perform such determination, it is only necessary to set an impedance value $Z_{th2}$ (specifically larger than 60Ω, for example 1000Ω) as a second reference value. Further, it may also be configured such that when the impedance value acquired by the measurement is an impedance value between $Z_{th}$ and $Z_{th2}$, the control section 35 determines that the impedance value acquired by the measurement is within the predetermined range, so as to enable the paired electrodes corresponding to the case to be used as the paired electrodes which are used at the time when the actual treatment is performed.

Further, the control section 35 stores the determination result, for example, in the switch section control table 42. In this case, a determination result storage area 42a for storing the determination result is provided in the switch section control table 42. Note that the determination result is shown in the determination result column in FIG. 5, and hence the determination result storage area is described as the determination result column in the flow chart shown in FIG. 6.

It may also be configured such that when the determination result is stored, the determination result is stored not in the switch section control table 42 but, for example, in the memory 43.

In the case where the determination result is not stored in the determination result storage area 42a of the switch section control table 42, even when it is not selected by the selection switch 28b that the electrode setting operation mode is performed, the control section 35 requires, as a default setting, confirmation of whether or not the electrode setting operation mode is performed.

For example, when the initial setting, such as the setting of a high frequency power value, by the power set button 28a, is completed to establish a state in which the treatment can be performed, the control section 35 determines whether or not the determination result is stored in the determination result storage area 42a. When the determination result is not stored in the determination result storage area 42a, the control section 35 displays in the display section 29 that the determination result is not stored in the determination result storage area 42a, and requires confirmation of whether or not the electrode setting operation mode is performed.

Next, with reference to a flow chart shown in FIG. 6, the control steps of the electrode setting operation mode will be described at the time when a high frequency operation is performed on the basis of the present embodiment.

As shown in FIG. 1, the operator connects the high frequency treatment instrument 2 to the high frequency power supply apparatus 3, and turns on the power switch 26. Then, the operator performs the initial setting in step S1. At the time of the initial setting, the operator sets a high frequency power value, and the like. Also, the operator selects an operation mode. In this case, description will be given assuming that the operator selects, by the selection switch 28b, the case where, after a set of paired electrodes is automatically selected by the electrode setting operation mode, the paired electrodes are operated in the treatment operation mode.

Then, the control section 35 performs, as shown in step S2, control to set the high frequency power value to a value sufficiently smaller than the high frequency power value for treatment set at the time of the initial setting, (for example, to a state in which the high frequency power is supplied by a high frequency signal having a small amplitude and small current value (constant current value)), so as to thereby start the electrode setting operation mode from step S2 to step S18.

Note that the high frequency current to be applied is preferably set in step S2 to a sufficiently small level of electric power (for example, about 5 W) at which tissue degeneration is substantially prevented. This is because in order to determine a set of paired electrodes used for the treatment, the high frequency current is made to flow between the paired electrodes, and hence because the high frequency power is set to a level small enough to thereby make it possible to prevent the unnecessary living tissue degeneration and scorching of blood.

The operator grasps the operation section 5 of the high frequency treatment instrument 2 to hold the living tissue as the treatment object by increasing a distance between the treatment members 16a and 16b which are provided at the distal end of the high frequency treatment instrument 2 and which are freely opened and closed. Then, as shown in step S3, the operator operates the handles 12a and 12b of the operation section 5 so as to close the treatment member 16a and 16b and thereby grasps the living tissue by the treatment members 16a and 16b.

After grasping the living tissue, the operator depresses (turns on) the foot switch 27, as shown in step S4. In response to the operation signal, the control section 35 supplies the high frequency power to the side of the high frequency treatment instrument 2 from the high frequency power supply apparatus 3 via the cable 4. When supplying the high frequency power, the control section 35 supplies the high frequency power in synchronization with the selection of a set of paired electrodes which are turned on according to the following procedure in the switch section control table 42.

First, in step S5, the control section 35 sets the parameter I of the procedure number to the initial value of 1 (I=1). Then, in step S6, the control section 35 refers to the information of the procedure No. 1 in the switch section control table 42 (in FIG. 6, simply abbreviated as control table). Then, in the following step S7, the control section 35 selects the switches of the switch sections 41a and 41b according to the information of the procedure No. 1. In this case, only the switches Sa-1 and Sb-1 are selected so as to be closed (turned on) (other switches are turned of).

Then, as shown in step S8, the power is supplied to the side of the electrodes a-1 and b-1 from the power supply section 31. Thus, the high frequency current is made to flow into the side of the electrodes a-1 and b-1.

In this case, as shown in step S9, the impedance measuring section as the biological information measuring section 38 receives the measured values of the voltage sensor 37 and the current sensor 39, and calculates an impedance value. Then, in the following step S10, the control section 35 acquires the impedance value calculated from the measured values, and determines whether or not the impedance value is equal to or greater than the determination impedance value Zth (specifically 40Ω).

When determining that the measured impedance value is 40Ω or more, the control section 35 determines in step S11 that only a living tissue as the treatment object exists between the paired electrodes (a-1 and b-1 as I=1 in this case) connected to the paired switches which are turned on, or that the living tissue does not exist between the paired electrodes. Then, the control section 35 determines the measurement result at this time as "OK", and stores the determination result in the determination result column of the procedure No. 1 in the switch section control table 42.

On the other hand, when determining in the determination processing in step S10 that the measured impedance value is less than 40Ω, the control section 35 determines in step S12 that blood exists between the paired electrodes. Then, the control section 35 determines the measurement result at this time as "NG", and stores the determination result in the determination result storage area of the procedure No. 1 in the switch section control table 42.

In the following step S13, the control section 35 increments the parameter I by 1. Further, in the following step S14, the control section 35 determines whether or not the parameter I>3. When the condition that the parameter I>3 is not satisfied, the control section 35 returns to the processing in step S6.

Then, in this case, the control section 35 similarly performs the processing from step S6 to step S12 in the state where the parameter I=2. In step S13, the control section 35 sets the parameter I to 3. After performing the determination processing in step S14, the control section 35 similarly performs the processing from step S6 to step S12.

In this way, the control section 35 acquires the determination results for all the selected sets of paired switches in the switch sections 41a and 41b. In other words, the control section 35 acquires, for all the sets of paired electrodes, the determination result information on whether or not a living tissue, which is not the treatment object, exists between the each set of paired electrodes.

Thereafter, since the parameter I is set to 4 in step S13, the control section 35 shifts to the processing in step S15 as a result of the determination processing in step S14.

In step S15, the control section 35 determines whether or not at least one result determined as "OK" is stored in the determination result storage area 42a of the switch section control table 42. Then, when determining that one or more results determined as "OK" exist, the control section 35 turns on (closes) in step S16 all the sets of paired switches which are determines as "OK". Then, the control section 35 sets the paired electrodes connected to the paired switches, as the bipolar electrode for actually performing the treatment.

Further, the control section 35 sets the power value to the value set at the time of initial setting.

Then, in the following step S17, the control section 35 displays in the display section 29 that the electrode setting operation mode is normally completed, in other words, that the setting of the bipolar electrode suitable for performing the treatment is completed. Further, the control section 35 may also be configured to display in the display section 29 that the high frequency power is supplied to the side of the set bipolar electrode, so as to thereby continue the treatment by the supplied high frequency current.

Then, the control section 35 supplies in step S19 the high frequency power of the set value (set in the treatment operation mode) to the side of the bipolar electrode, and performs the treatment by making the high frequency current flow to the living tissue which is made conductive with the bipolar electrode.

In this way, when the electrode setting operation mode is normally completed, even in the state where blood exists between a set of paired electrodes, the set of paired electrodes is set to the state where the high frequency current is prevented from flowing through the set of paired electrodes. Thus, when the treatment operation mode is performed in this state, the operator is able to smoothly perform the treatment by making the high frequency current flow only through the living tissue as the treatment object.

On the other hand, when determining in the determination in step S15 that no result determined as "OK" is stored, the control section 35 displays in step S18 an error message in the display section 29. Then, the control section 35 stops or inhibits the operation to supply the high frequency power for treatment from the power supply section 31 to the side of the high frequency treatment instrument 2.

Note that the control section 35 may also be configured so as to more specifically display the contents of the error at the time when displaying the error message. Specifically, the control section 35 may also be configured so as to display a message that blood exists between the paired electrodes of all the three sets of paired electrodes, and that even when the combination of the switches which are turned on in the switch sections 41a and 41b is changed, it is difficult to prevent the scorching and sticking of blood (because a large high frequency current is made to flow into the blood portion).

The typical operation contents according to the present embodiment are explained with reference to FIG. 6, and the operation contents will be more specifically described with reference to a drawing showing a state on the side of the treatment section 8, and the like.

FIG. 7 shows a specific example in which, in step S3 shown in FIG. 6, the living tissue as the treatment object is grasped by the operator with the treatment section 8 at the distal end of the high frequency treatment instrument 2.

In the example shown in FIG. 7, a state is shown where a blood vessel 51 which is the living tissue as the treatment object is grasped at the central portion of the bipolar electrode section 9, and where blood 52 is adhered to the distal end portion of the bipolar electrode section 9. Further, the description will be given by assuming that the impedance value of the blood 52 is 20Ω and that the impedance value of the blood vessel 51 is 60Ω.

Subsequently to step 3 and after turning on the foot switch 27 in step 4 and setting the parameter I, the control section 35 closes, in step S6 and step S7, the switch contacts so as to turn on only the set of paired switches Sa-1 and Sb-1 according to the information of the procedure No. 1 in the switch section control table 42. Thereby, the high frequency current is made to flow through the paired electrodes a-1 and b-1 connected to the paired switches Sa-1 and Sb-1 as shown in step S8.

In this state, the impedance measuring section 38a which configures the biological information measuring section 38 calculates an impedance.

In the case of the example shown in FIG. 7, nothing is grasped between the paired electrodes a-1 and b-1, and hence the measured impedance value becomes infinite. FIG. 8 schematically shows an electrical equivalent circuit in this state. Note that in FIG. 8 to FIG. 11, the paired electrodes a-1 and b-1, the paired electrodes a-2 and b-2, the paired electrodes a-3 and b-3 in FIG. 7 are shown as the first paired electrodes, the second paired electrodes, and the third paired electrodes, respectively.

In the case where the impedance value becomes infinite, the impedance value is determined as 40Ω or more in the determination in step S10, and "OK" is stored in the determination result column of the switch section control table 42.

Then, according to the procedure No. 2 in the switch section control table 42, the control section 35 closes the switch contacts so as to turn on only the set of paired switches Sa-2 and Sb-2.

Figure 9:
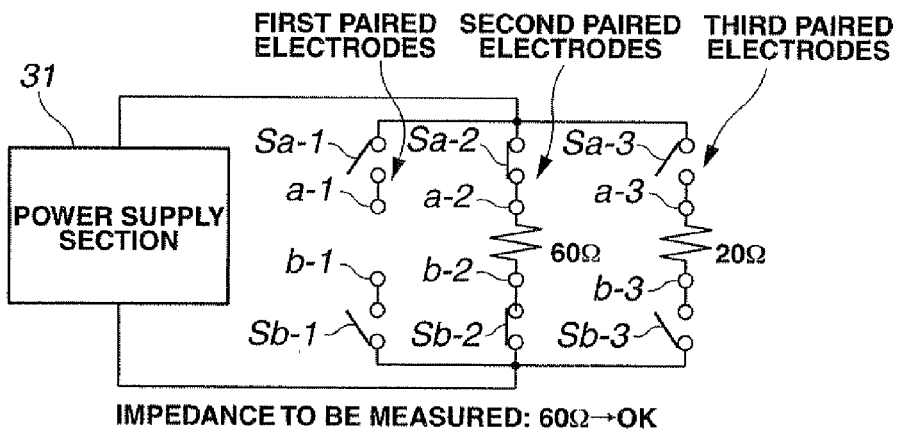
FIG. 9 is a figure showing an equivalent circuit in the case where an impedance is measured by a second paired electrodes in the state shown in FIG. 7.

Only the blood vessel 51 which is the living tissue as the treatment object is grasped between the paired electrodes a-2 and b-2 connected to the paired switches of Sa-2 and Sb-2, that is, between the second paired electrodes. Thus, the measured impedance value becomes 60Ω, so that "OK" is stored as the result of the measurement. FIG. 9 schematically shows an electrical equivalent circuit in this state.

Figure 10:
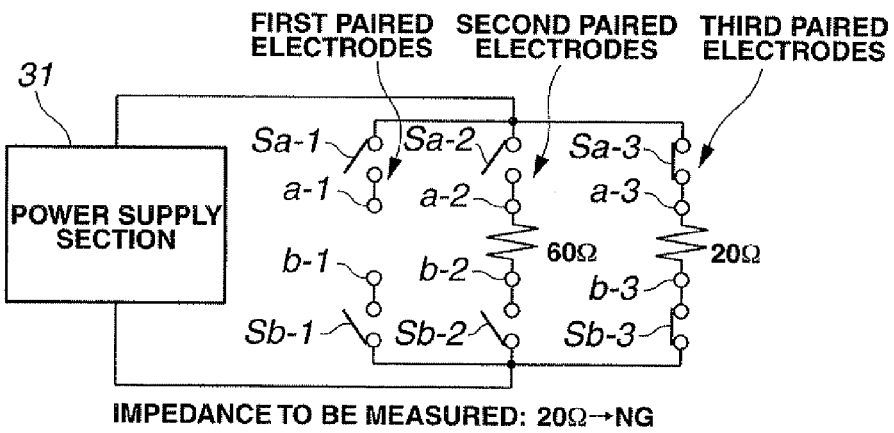
FIG. 10 is a figure showing an equivalent circuit in the case where an impedance is measured by a third paired electrodes in the state shown in FIG. 7.

Similarly, according to the procedure No. 3 in the switch section control table 42, the control section 35 closes the switch contacts so as to turn on only the set of paired switches Sa-3 and Sb-3. Only the blood 52 is adhered to the portion of the paired electrodes a-3 and b-3 respectively connected to the paired switches of Sa-3 and Sb-3, that is, to the portion of the third paired electrodes. Thus, the measured impedance value becomes 20Ω, so that "NG" is stored as the result of the measurement. FIG. 10 schematically shows an electrical equivalent circuit in this state.

Figure 11:
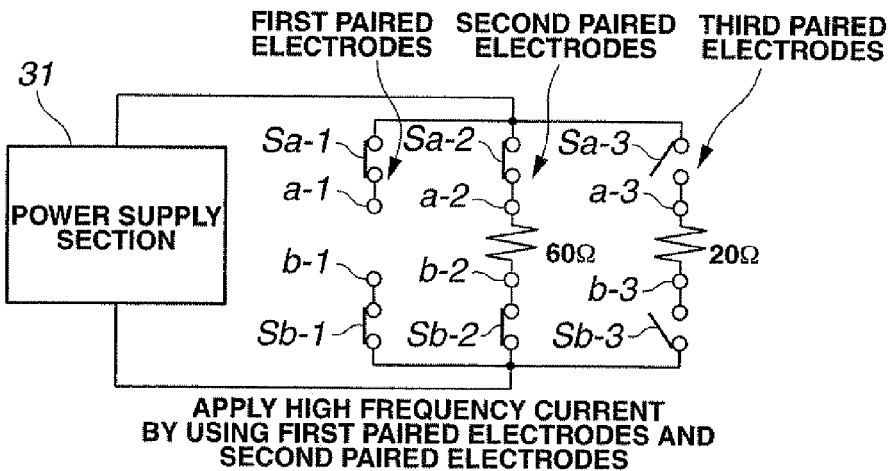
FIG. 11 is a figure showing an equivalent circuit in the case where a high frequency treatment is performed by using the first paired electrodes and the second paired electrodes in the state shown in FIG. 7.

As a result of the above described measurement, it is eventually determined so as to adopt the state where the switches Sa-1 and Sa-2, and the switches Sb-1 and Sb-2 are turned on as shown in FIG. 11, that is, to adopt the first paired electrodes and the second paired electrodes as the bipolar electrodes at the time when the treatment is actually performed. In this state, the high frequency current is applied on the basis of the high frequency power value set by the power setting section 36.

In this way, when the operation method of applying the high frequency current through step S1 to step S17 in FIG. 6 is adopted, it is possible to prevent the high frequency current from being applied to the paired electrodes to which the blood 52 is adhered, and possible to prevent the phenomenon that the blood 52 is scorched and stuck to the electrode section.

That is, it is possible to prevent the high frequency current from being applied to the paired electrodes to which the blood 52 is adhered, and possible to prevent the blood 52 from being scorched and stuck to the electrode section, in such a way that the high frequency current is applied only to the portion of the paired electrodes at which the measured impedance value is a certain fixed value or more, by utilizing the fact that the impedance value of the blood 52 is smaller than the impedance value of the living tissue as the treatment object.

In this way, the present embodiment has effects of preventing the high frequency current from being applied to the electrodes to which the blood 52 is adhered, and of preventing the blood from being scorched and stuck to the electrode section.

Note that the value of 40Ω specifically shown as the threshold value in step S10 as described above, is a specific example, and other values may also be used as the threshold value. The threshold value of impedance of the living tissue as the treatment object and the threshold value of impedance of the blood (as a living tissue which is not the treatment object), which are used for the determination in this way, may be set from standard values obtained in the case where the impedance values of the living tissue and the blood are measured beforehand by the high frequency treatment instrument 2 actually used for the treatment. Then, the threshold values set from the standard values may be stored in the memory 43, or the like.

Second Embodiment

Figure 12:
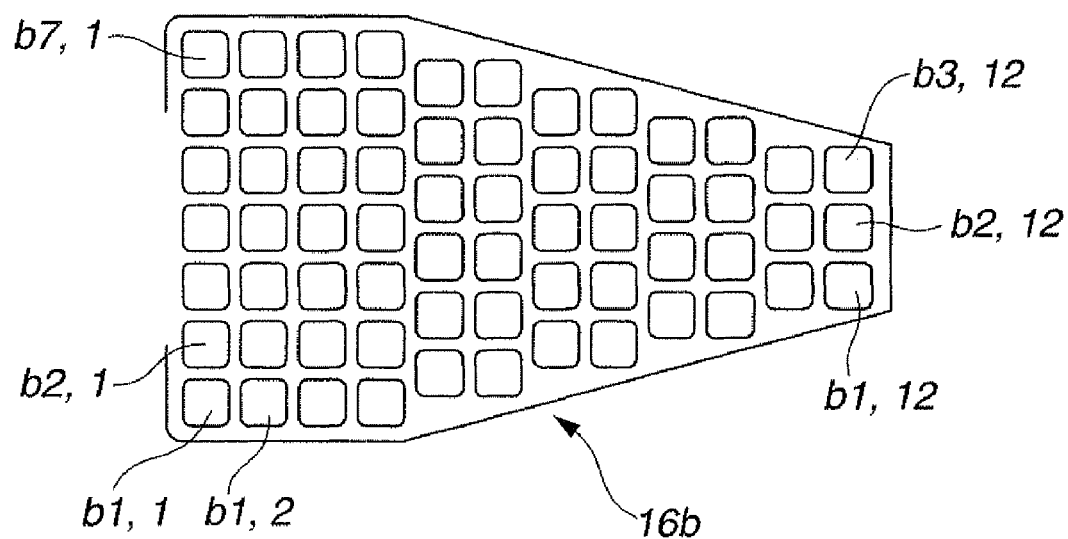
FIG. 12 is a plan view showing shapes of a plurality of two-dimensionally arranged electrodes which are provided on one of the treatment members configuring a treatment section according to a second embodiment of the present invention.

Next, a second embodiment according to the present invention will be described with reference to FIG. 12 and FIG. 13. FIG. 12 shows an arrangement example of a plurality of electrodes provided, for example, on the treatment member 16$b$ adopted for the high frequency treatment instrument of the present embodiment.

In the first embodiment, a plurality of electrodes b-1 to b-3 are arranged in the longitudinal direction of the treatment member 16$b$. On the other hand, in the present embodiment, a plurality of electrodes bi, j are two-dimensionally arranged in the longitudinal direction of the treatment member 16$b$ and the direction perpendicular (referred to as the width direction) to the longitudinal direction.

In FIG. 12, only typical electrodes are denoted by reference characters of b1, 1, b2, 1, . . . , b7, 1, b2, 1, . . . , b1, 12, b2, 12, b3, 12.

Note that signal lines (not shown) are respectively connected to electrodes bi, j. Further, the each signal line is connected to each switch which configures a switch section (not shown), and ON/OFF of the each switch can be selected by the control section 35.

Note that the treatment member 16$a$ also has the same configuration as that of the treatment member 16$b$ shown in FIG. 12. In the present embodiment, the plurality of electrodes bi, j are two-dimensionally arranged so as to two-dimensionally form a plurality of sets of paired electrodes bi, j, and the area of each electrode bi, j is made smaller than the area of the electrode in the first embodiment.

Thus, the determination accuracy by the determining section in the first embodiment is further improved. That is, in the first embodiment, for example in the state as shown in FIG. 7, when the blood 52 is adhered in a small area region of the paired electrodes a-3 and b-3 (for example, in a region having an area of ⅓ or less of the area of the electrode), the measured impedance value may be determined to be 40Ω or more as the determination result in step S10 shown in FIG. 6.

The present embodiment is configured such that the determination with higher accuracy can be performed by reducing the electrode area.

That is, the ratio of the electrode area, at which the living tissue as the treatment object and the living tissue which is not the treatment object can be properly determined, is increased by reducing the electrode area. More specifically, for example, the electrode b-3 shown in FIG. 7 corresponds to about ten electrodes in FIG. 12.

In the case of the electrode b-3 shown in FIG. 7, as described above, when the blood is adhered, for example, in the area of about ⅓ or less of the area of the electrode, it may be erroneously determined that no blood is adhered to the electrode b-3.

On the other hand, in the case of the configuration shown in FIG. 12, some (a few) electrodes among ten electrodes may be erroneously determined in such case, but most of the other electrodes can be properly determined.

That is, according to the present embodiment, the determining function can be more improved than the first embodiment.

Further, in the present embodiment, for example, a sensor 61 is provided, which is configured to detect a distance between the electrode pairs of the treatment members 16$a$ and 16$b$ in the state in which the living tissue as the treatment object is grasped between the treatment members 16$a$ and 16$b$.

The sensor may be configured so as to be attached to the member which is moved to open and close the treatment members 16$a$ and 16$b$ by the operation of the handles 12$a$ and 12$b$ in the high frequency treatment instrument 2 shown in FIG. 1. The sensor 61 may also be configured so as to be attached, for example, to the pivotal support section 14 and to thereby detect the above described distance by detecting the rotation amount between the handles 12$a$ and 12$b$.

Figure 13:
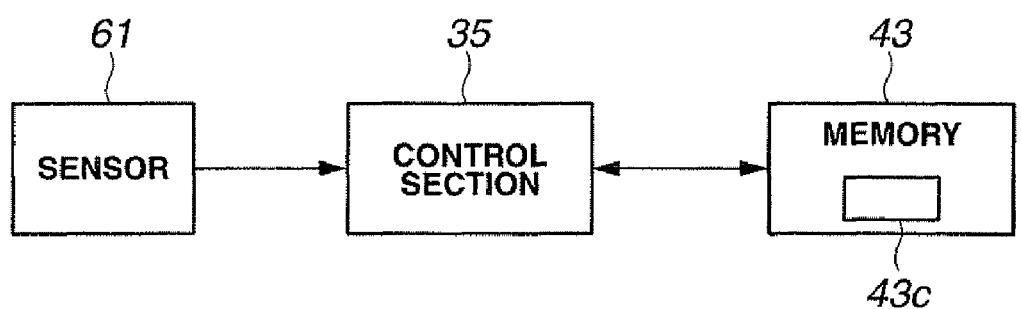
FIG. 13 is a block diagram showing a configuration in which a reference value used at the time of determination is changed to be set on the basis of a detection signal of a sensor for detecting a distance between the paired electrodes.
Figure 14:
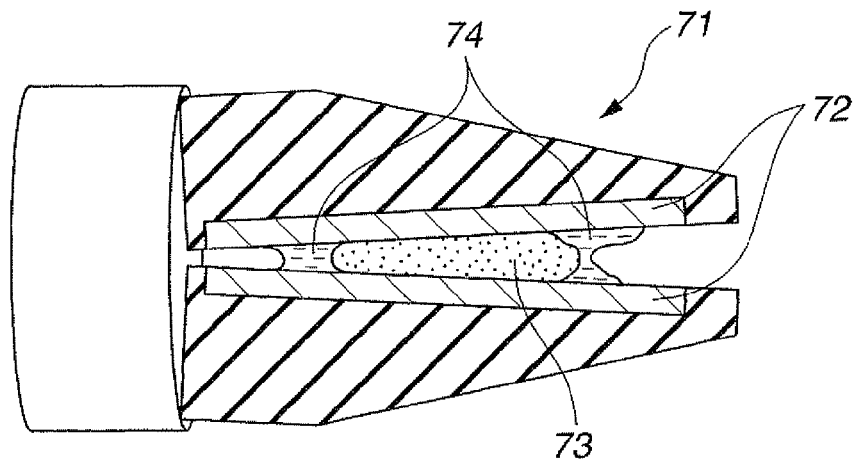
FIG. 14 is a figure showing, by a use example, a treatment section provided with a bipolar electrode in a preceding example.
Figure 15:
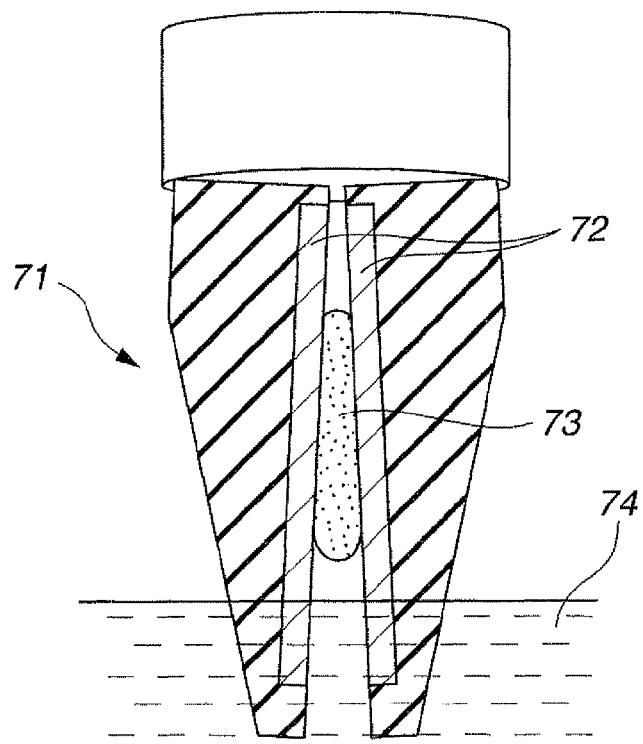
FIG. 15 is a figure showing, by another use example, the treatment section provided with the bipolar electrode in the preceding example.

The detection signal of the sensor 61 is inputted into the control section 35 as shown in FIG. 13. Further, in a look-up table (hereinafter abbreviated as LUT) 43$c$ formed, for example, in a storage area in the memory 43 are stored an average value of the distance between the paired electrodes of the treatment members 16$a$ and 16$b$ with respect to the detection signal of the sensor 61, and an impedance value as a reference value, on the basis of the average value, to the determine whether or not the living tissue is the treatment object.

That is, when the reference value, on the basis of which the living tissue as the treatment object is distinguished from the living tissue which is not the treatment object, is set in correspondence with the distance between the paired electrodes, the determination can be more accurately performed.

In the present embodiment, a distance between the paired electrodes is detected, and thereby a reference value is set in correspondence with the detected distance. Thus, it is configured such that the determination can be more accurately performed. Further, it is configured such that a reference value can be set in correspondence with a value of the electrode area.

When the operator turns on the foot switch 27, the control section 35 in the present embodiment receives the detection signal of the sensor 61 at this time, and reads the reference value corresponding to the average value of the distance between the paired electrodes from the LUT 43$c$. Then, the control section 35 performs the determination in step S10 shown in FIG. 6 by using the reference value.

The other configuration in the present embodiment is the same as that of the first embodiment. According to the present embodiment, it is possible to more accurately perform the determination whether or not the living tissue which is not the treatment object exists between the paired electrodes. The other effects of the present embodiment are the same as those of the first embodiment.

In the present embodiment, it can also be said that when the living tissue as the treatment object is grasped between the treatment members 16a and 16b, it is possible to measure and determine the two-dimensional distribution of the paired electrodes in contact with the living tissue which is the treatment object and the two-dimensional distribution of the paired electrodes in contact with the living tissue which is not the treatment object. Also in the first embodiment, the longitudinal distribution, that is, the one-dimensional distribution of the paired electrodes can be measured and determined by increasing the number of electrodes in the longitudinal direction.

Note that in the above description, a measured impedance is described as an example of the biological information, but a measured resistance value may also be used instead of the impedance value. Also in this case, almost the same effects can be obtained.

Having described the preferred embodiments of the invention referring to the accompanying drawings, it should be understood that the present invention is not limited to those precise embodiments and various changes and modifications thereof could be made by one skilled in the art without departing from the spirit or scope of the invention as defined in the appended claims.

What is claimed is:

1. A high frequency operation apparatus comprising:
a treatment section configured to perform a treatment of a living tissue as a treatment object, the treatment section having first and second paired treatment members with facing surfaces configured to open and close;
a sensor configured to detect a distance between the first and second treatment members in a state where the living tissue as the treatment object is grasped by the first and second treatment members;
a plurality of electrodes provided at the treatment section;
a switch section connected to each of the plurality of electrodes and configured to switch between conduction and cut off of the plurality of electrodes so as to configure paired electrodes from the plurality of electrodes;
a power supply section configured to supply high frequency power to the living tissue via the switch section and the paired electrodes which are made conductive by the switch section;
a biological information measuring section configured to sequentially measure biological information of the living tissue in the case where a plurality of different sets of paired electrodes are formed and where the high frequency power is supplied from the power supply section via the each set of the plurality of sets of the electrode pairs by the switching of the switch section;
a determining section configured to determine, by referring to a reference value, whether or not the measured values of the biological information, which are measured for the plurality of sets by the biological information measuring section, are within a predetermined range;
a reference value storing section configured to store the reference values which are different according to information on the distance between the first and second paired treatment members; and
a control section configured to control the power supply section to supply the high frequency power to the living tissue by using, as a bipolar electrode, only the paired electrodes corresponding to the measure value determined by the determining section as being within a predetermined range.

2. The high frequency operation apparatus according to claim 1, wherein when the biological information measuring section sequentially measures the biological information by the switching of the switch section, the control section sets the high frequency power supplied to the living tissue by the power supply section to a small value of high frequency power which does not cause the living tissue to degenerate.

3. The high frequency operation apparatus according to claim 1, wherein a plurality of first and second electrodes are respectively provided, as the plurality of electrodes, on the facing surfaces of the first and second treatment members, and wherein the paired electrodes of the plurality of different sets of paired electrodes are configured by one set of facing first and second electrodes of the plurality of first and second electrodes.

4. The high frequency operation apparatus according to claim 1, wherein the biological information measuring section is an impedance measuring section configured to measure an impedance value of the living tissue.

5. The high frequency operation apparatus according to claim 1, wherein the biological information measuring section is a resistance measuring section configured to measure a resistance value of the living tissue.

6. The high frequency operation apparatus according to claim 1, wherein the reference value is set as a threshold value between a standard value of biological information represented by the living tissue as the treatment object, and a standard value represented by a living tissue having a larger high frequency loss for the supply of high frequency power than the living tissue as the treatment object, and wherein when comparing the measured value with the threshold value and determining that the measured value is closer to the standard value of the biological information represented by the living tissue as the treatment object than the threshold value, the determining section determines that the measured value is within the predetermined range.

7. The high frequency operation apparatus according to claim 1, wherein the reference value is set as a threshold value between a standard value of biological information represented by the living tissue as the treatment object, and a standard value represented by blood having a larger high frequency loss for the supply of high frequency power than the living tissue as the treatment object, and wherein when comparing the measured value with the threshold value and determining that the measured value is closer to the standard value of the biological information represented by the living tissue as the treatment object than the threshold value, the determining section determines that the measured value is within the predetermined range.

8. The high frequency operation apparatus according to claim 1, further comprising: a storing section of table data formed by tabulating switching control contents, according to which the switching of a plurality of switch elements connected to each of the plurality of electrodes in the switch section is controlled so as to sequentially form a plurality of different sets of paired electrodes.

9. The high frequency operation apparatus according to claim 1, further comprising: a reference value storing section configured to store information of the reference value used for the determination by the determining section.

10. The high frequency operation apparatus according to claim 1, wherein the treatment section includes paired first and second treatment members having facing surfaces which are opened and closed, and wherein a plurality of first and second electrodes are respectively provided on the facing surfaces of the first and second treatment members so that the plurality of electrodes are two-dimensionally arranged.

11. The high frequency operation apparatus according to claim 1, wherein the first and second treatment members are provided at the distal end of the high frequency treatment section which performs an opening or closing operation of the first and second treatment members.

12. A high frequency operation method for performing a high frequency operation to a living tissue by selectively setting a bipolar electrode used for treatment from a plurality of sets of paired electrodes respectively provided on a pair of treatment members which are provided at a distal end of a high frequency treatment instrument and which are opened and closed, the treatment instrument having a sensor configured to detect a distance between the first and second treatment members in a state where the living tissue as the treatment object is grasped by the first and second treatment members, the high frequency operation method comprising:
  a grasping step of grasping a living tissue as a treatment object by the pair of treatment members;
  an electrode selection step, performed by a switch section, of sequentially selecting a set of paired electrodes from the plurality of sets of paired electrodes which are respectively provided on the mutually facing surfaces of the pair of treatment members;
  a power supply step, performed by a power supply section, of supplying high frequency power to the living tissue which is grasped by the pair of treatment members, via the sequentially selected one set of paired electrodes;
  a biological information measurement step, performed by a biological information measuring section, of sequentially measuring biological information at the time when the high frequency power is supplied via the sequentially selected one set of paired electrodes;
  a determination step, performed by a determining section, of determining whether or not the value of the sequentially measured biological information is within a predetermined range, by a comparison with a reference value; and
  a control step, performed by a control section, of controlling the power supply section to supply the high frequency power to the living tissue by using, as one bipolar electrode, only the paired electrodes corresponding to the measured value determined by the determination step as being within the predetermined range.

13. The high frequency operation method according to claim 12, wherein when the biological information is sequentially measured in the biological information measurement step, the high frequency power supplied to the living tissue is set to a small value of high frequency power which does not cause the living tissue to degenerate.

14. The high frequency operation method according to claim 12, wherein the biological information measurement step measures an impedance value or a resistance value of the living tissue.

* * * * *